Figure 1:
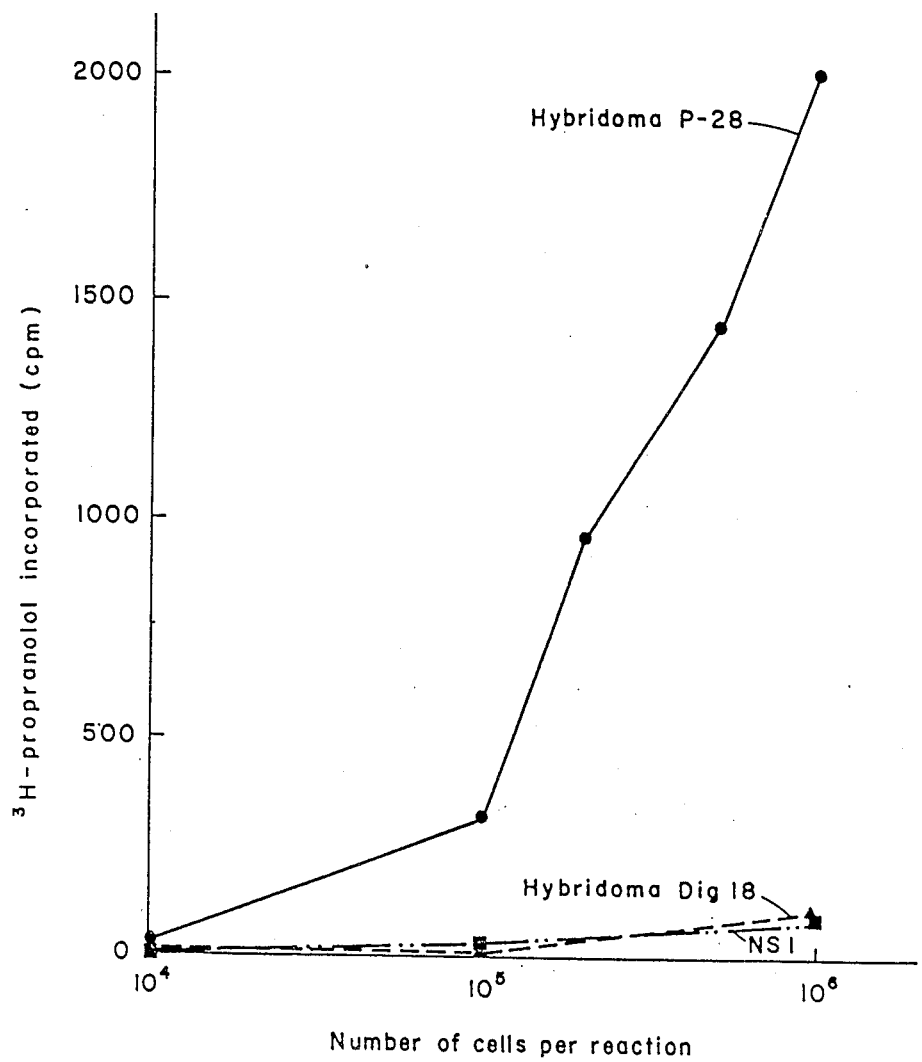

United States Patent [19]

Wang et al.

[11] Patent Number: 4,727,023

[45] Date of Patent: Feb. 23, 1988

[54] PREPARATIONS FOR USE IN SOLID PHASE IMMUNOASSAYS COMPRISING MONOCLONAL ANTIBODIES COVALENTLY EMBEDDED IN THEIR IMMOBILIZED HYBRIDOMA CELLS

[75] Inventors: Lynn Wang, Jerusalem; Michael Inbar, Mazkeret Batya, both of Israel

[73] Assignee: I.D.L. International Diagnostic Laboratories Limited, Jerusalem, Israel

[21] Appl. No.: 773,931

[22] Filed: Sep. 9, 1985

[30] Foreign Application Priority Data

Sep. 12, 1984 [IL] Israel .......................................... 72924

[51] Int. Cl.$^4$ ................... G01N 33/53; G01N 33/558; C12N 15/00
[52] U.S. Cl. ........................................ 435/7; 424/1.1; 435/172.2; 435/174; 435/240.27; 436/519; 436/547; 436/548; 436/804; 436/535; 935/110
[58] Field of Search ................... 435/182, 243, 260, 7, 435/172.2; 436/519, 535, 547; 424/1.1

[56] References Cited

U.S. PATENT DOCUMENTS 4,409,331 10/1983 Lim ........................................ 424/93

OTHER PUBLICATIONS

Taber's Cyclopedic Med. Dictionary (1973), Davis Co., Phila., Pa., p. F-25.

*Primary Examiner*—Sam Rosen
*Attorney, Agent, or Firm*—Browdy and Neimark

[57] ABSTRACT

A reagent for use in solid phase immunoassay diagnostics comprises a matrix of non-active hybridoma cells embedded with its self-produced, covalently bound, actively presented monoclonal antibodies.

The solid phase reagent according to the invention is prepared by incubating in vitro a culture medium containing active hybridoma cells capable of producing monoclonal antibodies, allowing the formation of antibodies to proceed, separating and washing said cells, resuspending the cells in a buffer solution, adding to the resulting suspension an inactivator substance capable of converting active hybridoma cells into the non-active state.

13 Claims, 8 Drawing Figures

PREPARATIONS FOR USE IN SOLID PHASE IMMUNOASSAYS COMPRISING MONOCLONAL ANTIBODIES COVALENTLY EMBEDDED IN THEIR IMMOBILIZED HYBRIDOMA CELLS

The present invention concerns monoclonal antibody preparations for use in solid phase immunoassays.

It has been known for some time (see George Köhler and Ceasar Milstein, ((1975) Nature, 256, 465) that hybridoma cell lines can be used for the production of monoclonal antibodies (McAb). The parents of such hybridomas are, on the one hand, myeloma cells and, on the other hand, lymphocytes such as spleen cells obtained from immunized animals, e.g. mice, and selected for their ability to produce a particular McAb. Accordingly, by definition hybridomas are hybrid-myelomas which have inherited from the parent myeloma the ability to grow in vitro and in vivo and from the parent lymphocyte the ability to produce monoclonal antibodies of a desired specificity.

Conventionally, monoclonal antibodies can be used for solid phase immunoassays when they are chemically combined with macro-molecular carrier substances such as polymers. This method has, however, the shortcoming that by the chemical combination of the monoclonal antibody with a carrier substance there occurs a chemical modification which may affect unfavourably the activity of the antibodies and the performance of the immunoassay. Also, the recovery of the monoclonal antibodies from the growth medium and the subsequent chemical reaction, are both time-and material-consuming operations.

In the following specification and claims the terms "active" and "non-active" will be used in conjunction with hybridoma cells. The term "active" is meant to signify a viable hybridoma cell culture that is growing and actively producing monoclonal antibodies. The term "non-active" is used to signify a killed hybridoma cell/monoclonal antibodies complex which no longer produces new antibody molecules nor retains any cell division capability.

In accordance with the present invention there is provided a reagent for use in solid phase immunoassay diagnostics comprising a matrix of non-active hybridoma cells which are embedded with and convalently bound to its self-produced, actively presented monoclonal antibodies.

If desired, the solid phase reagent according to the invention may also contain auxiliary substances for use in immunoassay such as a dye or colour indicator for colorimetric tests, enzymatic, fluorescent, luminescent or radioactive labelling materials, etc.

The solid reagent according to the invention may for example, be in the form of a powder, beads, pellets, tablets, aggregations and the like. It may, moreover, be mounted on solid supports such as sticks, strips, tubes, microplates, etc.

The invention also provides a process for the preparation of a solid reagent for use in diagnostic immunoassay, comprising incubating in vitro a culture medium containing active hybridoma cells capable of producing monoclonal antibodies, allowing the formation of antibodies to proceed, separating and washing said cells, resuspending the cells in a buffer solution, adding to the resulting suspension a fixture capable of converting active hybridoma cells into the non-active state (inactivator substance), thereby to produce an immobilized non-active hybridoma cells/monoclonal antibodies complex, and binding excessive free inactivator substance.

In order to inactivate the hybridoma cells to form the non-active, immobilized complex, various reagents may be used, such as bi- or multi-functional crosslinking reagents. Among others, aliphatic aldehydes have been found suitable, such as for example, glutaraldehyde.

The solid phase reagent according to the invention can be stored for long periods of time and used when required in assay systems such as radioimmunoassay (RIA), enzyme immunoassay (EIA), fluorescent immunoassay (FIA), luminescence immunoassay (LIA), colorimetric immunoassay, cytochemistry and cell sorting, agglutination, etc.

The solid phase McAb reagent according to the invention is based on a new concept of using the hybridoma cells themselves as a component of the assay system, which has never been proposed before. This has the advantage over known solid phase McAb reagents in that the antibodies are in their native form and in high concentration and accordingly, the reagent according to the invention is considerably more reliable and accurate than known solid phase McAb reagents. Also, the production of the reagent according to the invention is simpler and cheaper than the production of conventional solid phase McAb preparations.

In principle, for using a McAb reagent according to the invention for the determination of an antigen, the sample in which the amount of antigen is to be determined is incubated with the reagent, for example, together with a labelled antigen probe. The unlabelled antigen in the sample competes with the labelled antigen for the combination site of the McAb on the immobilized non-active hybridoma cells. The resulting antibody-antigen complex bearing cells are separated from their liquid environment by a single step following which the amount of labelled antigen in the complex is determined. This amount is inversely proportional to the quantity of antigen originally present in the sample. A relationship can be constructed using known amounts of antigens in control samples. Thus the concentration of the antigen in the unknown specimen can be calculated.

In some instances, a combination of a certain type of labelled antigen probes together with special instrumentation allow for the determination of antigen in the unknown sample in a one-step homogeneous immunoassay using the solid phase McAb reagent according to the invention. For example, the antigen to be determined in the sample is incubated with the McAb reagent together with a fluorescein-labelled antigen probe. The unknown antigen competes with the fluorescence-labelled antigen for the reaction sites on the McAb on the immobilized non-active hybridoma cells. The entire reaction mixture can then be analyzed by Fluorescence Flow Cytometry without further manipulations. As this type of instrument measures and records the fluorescent intensity of each single cell, resulting in an integrated fluorescence distribution profile of the entire population of cells in the reaction mixture, the amount of mean fluorescence found on these immobilized hybridoma cells according to the invention will be inversely proportional to the quantity of unknown antigen in the sample.

Figure 2:
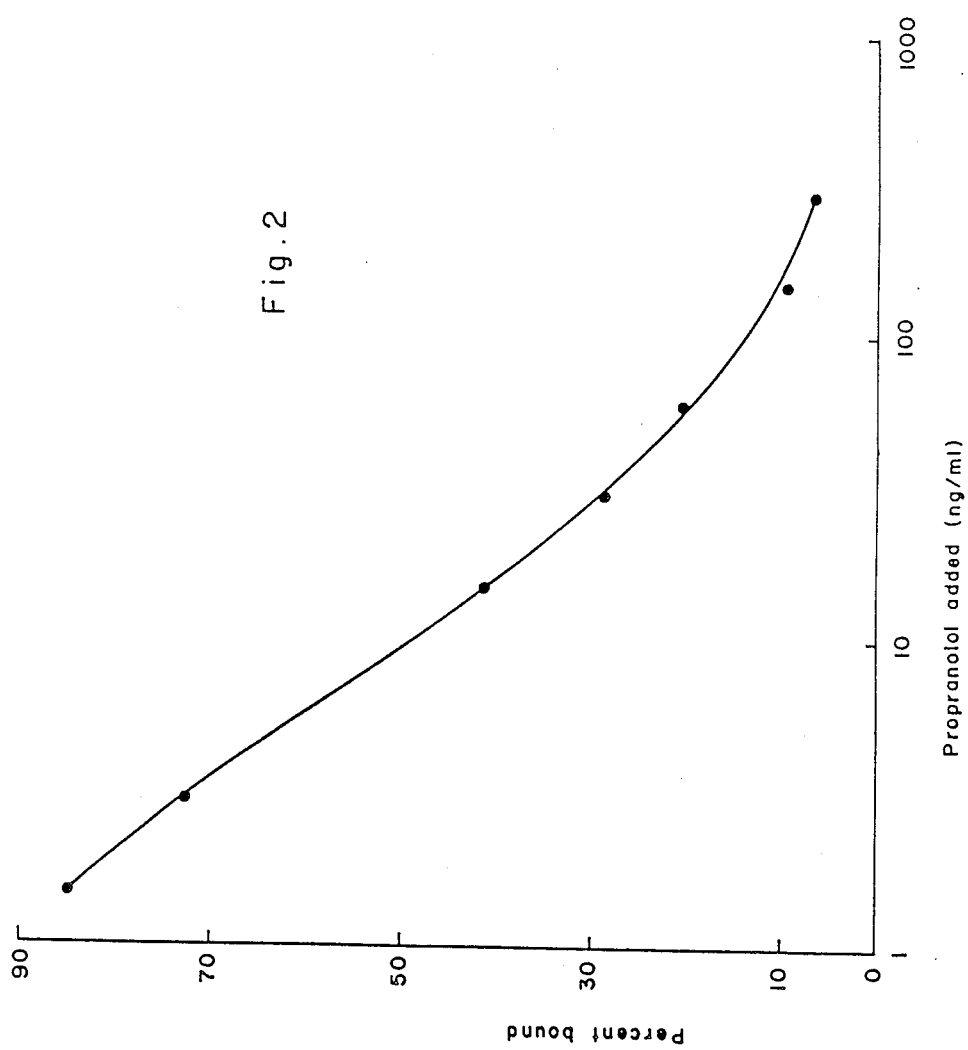
Figure 3:
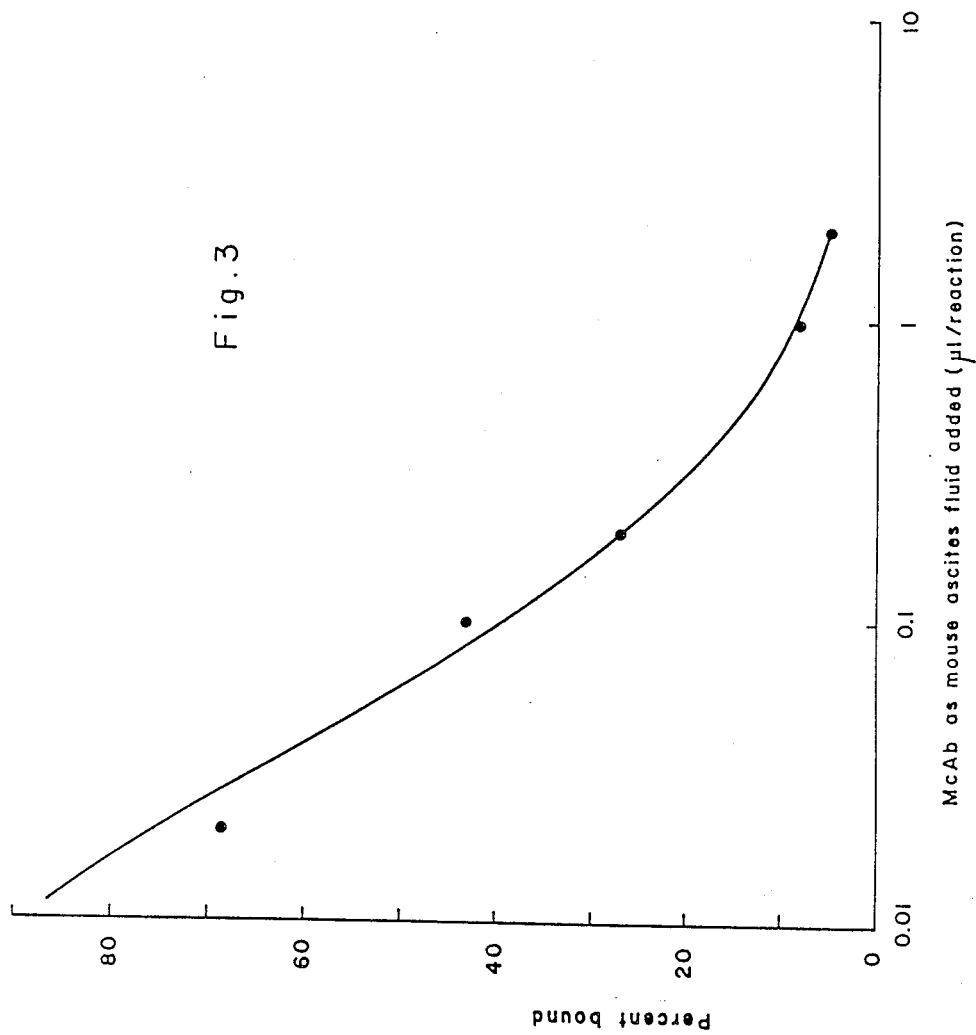
Figure 4:
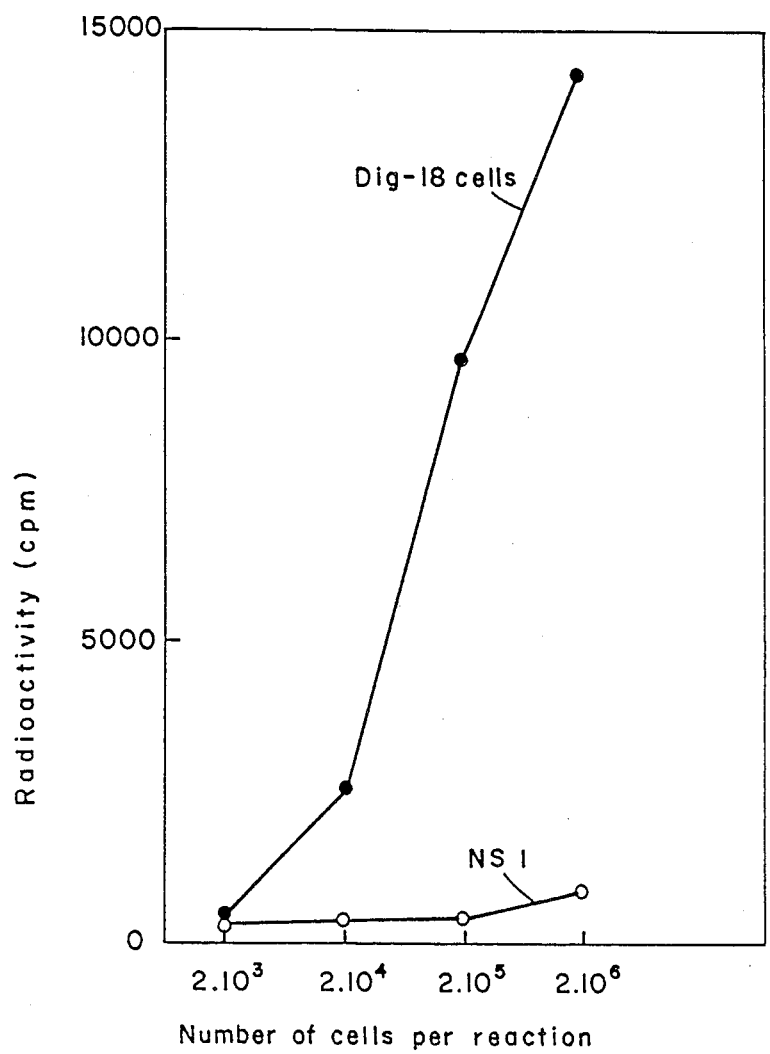
Figure 5:
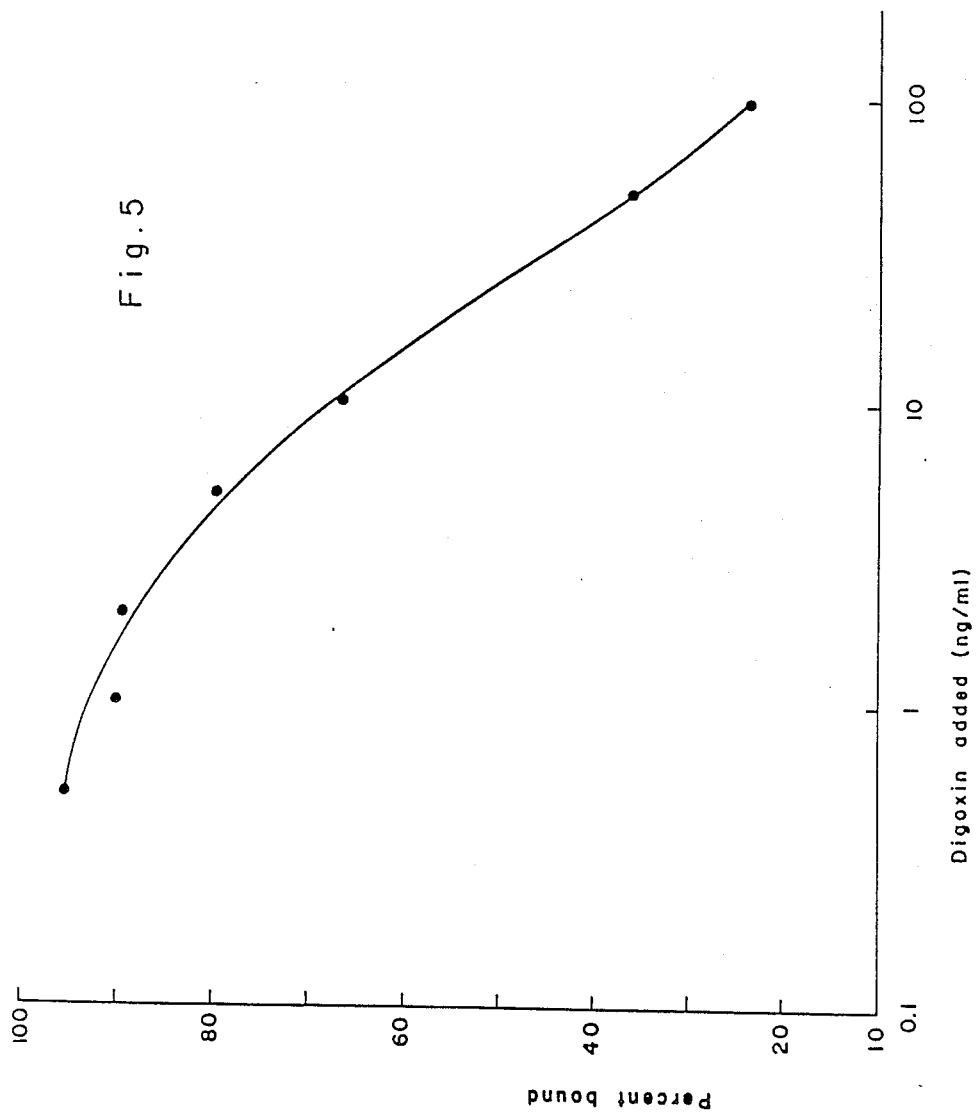
Figure 6:
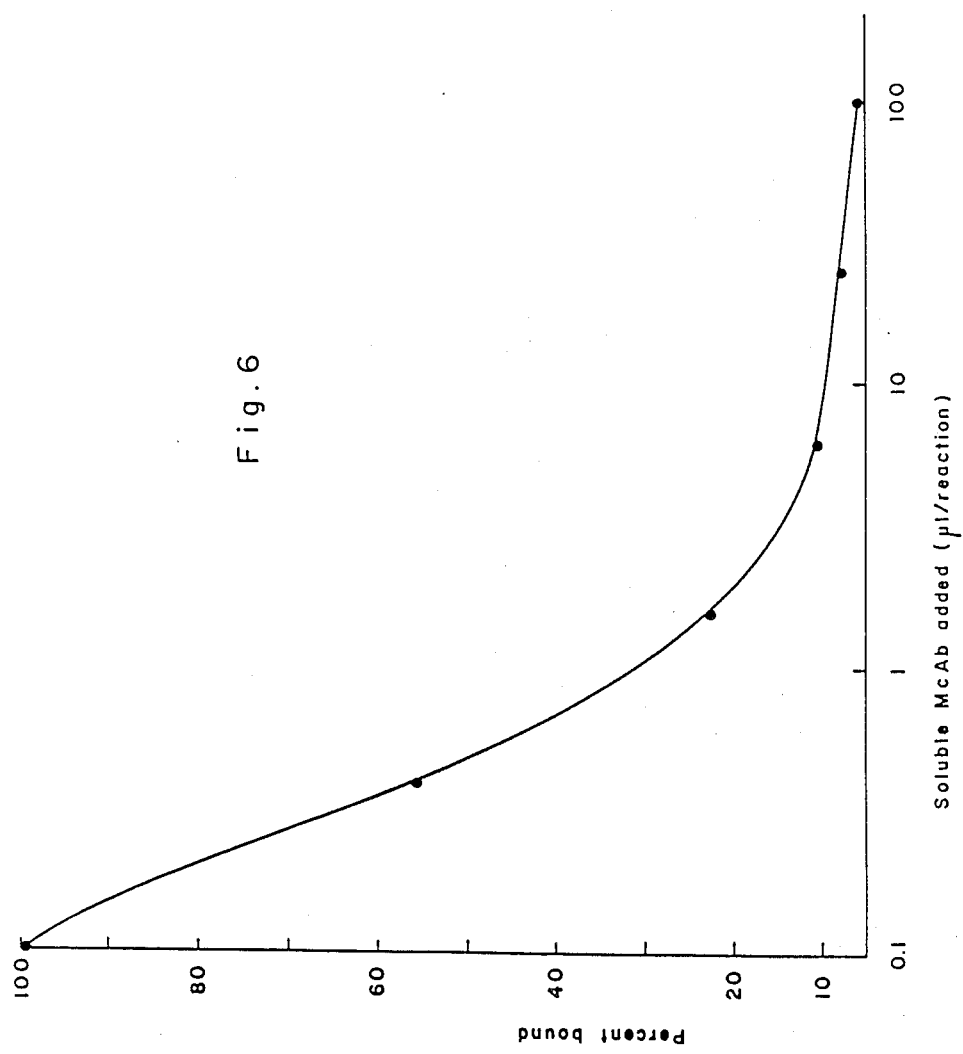

The invention will now be described with reference to the following examples and annexed drawings which are graphical representations showing the following:

FIG. 1—Specifity of binding of $^3$H-propranolol to a solid phase McAb reagent according to the invention;

FIG. 2—Dose response of an anti-propranolol solid phase McAb reagent according to the invention;

FIG. 3—Inhibition of the binding of $^3$H-propranolol to an anti-propranolol solid phase McAb reagent according to the invention by means of native free anti-propanolol McAb;

FIG. 4—Specificity of the binding $^{125}$I-digoxin by an anti-digoxin solid phase McAb reagent according to the invention;

FIG. 5—A standard curve of RIA assay for digoxin with an anti-digoxin solid phase McAb reagent according to the invention;

FIG. 6—Inhibition of the binding of $^{125}$I-digoxin with solid phase anti-digoxin McAb reagent according to the invention by means of a native free anti-digoxin McAb.

Figure 7:
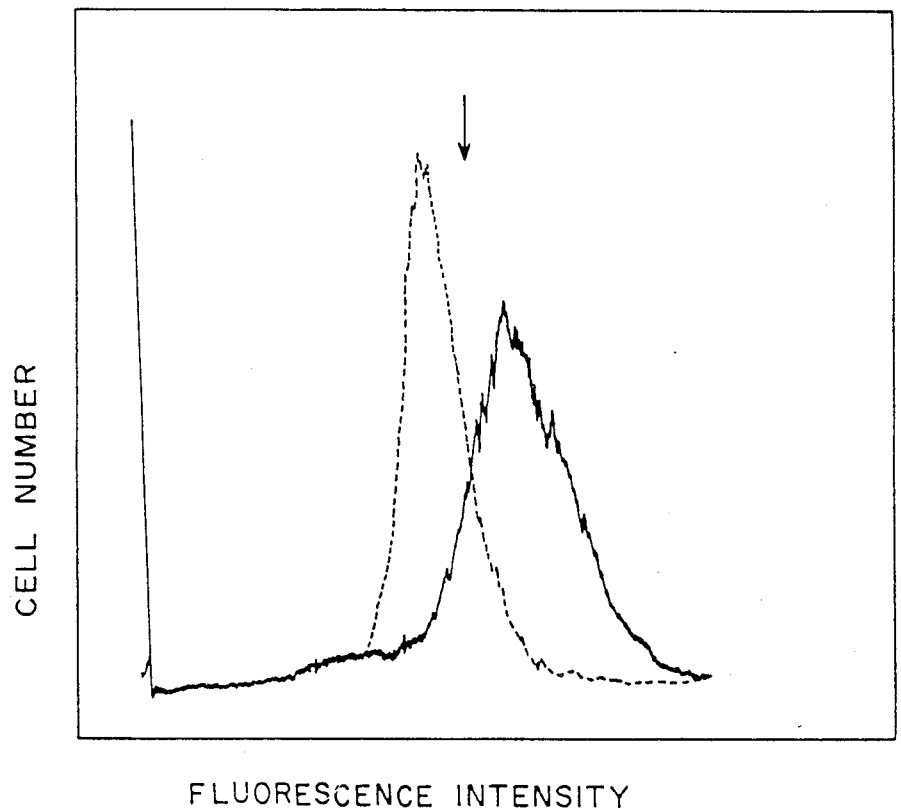
Figure 8:
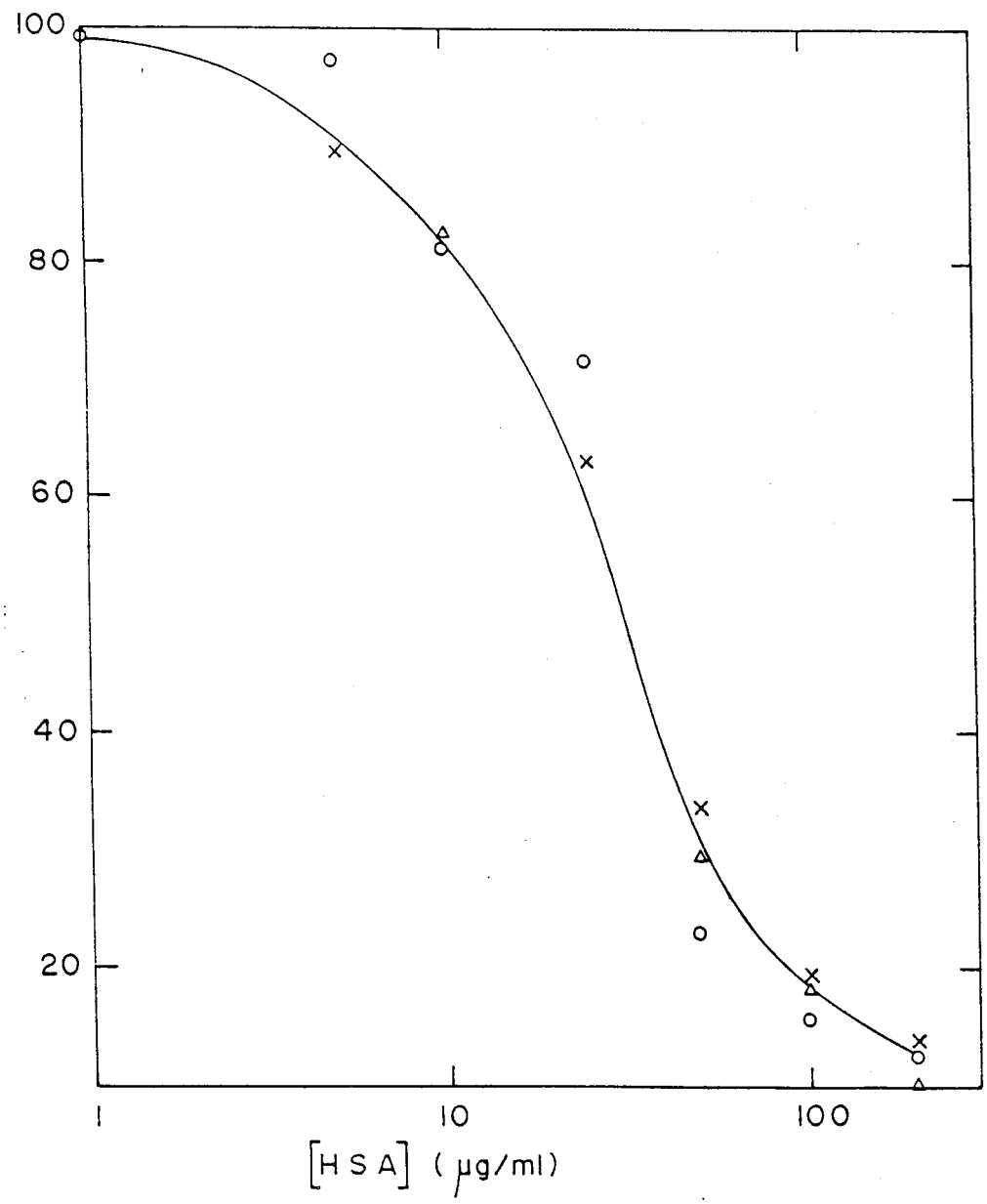

FIG. 7—Fluorescence flow cytometry curves of fixed B-20 cells. Unlabeled B-20 cells (left) and B-20 cells incubated with FITC-HSA (right). The arrow indicates the reference point described in the test. FIG. 8—Dose response curve of HSA using fixed B-20 cells, FITC-HSA and unlabeled HSA. Experiments were carried out on FACS and data summarizes 3 separate experiments as indicated by different symbols.

EXAMPLE 1. Preparation of non-active Hybridoma Cells - McAb Complex

Actively growing hybridoma cells were harvested by centrifugation and washed with serum free medium. The cells were resuspended in phosphate-buffer-saline (10 mM sodium phosphate pH 7.4, 150 mM sodium chloride) at $10^7$ cells per ml. Electronmicroscopically grade glutaraldehyde added to a final concentration of 2.5% (v/v). The reaction mixture was incubated at 4° C. for 30 minutes and glycine was added to a final concentration of 1M. After incubation for 10 minutes at 4° C. the suspension was centrifuged at 1200 RPM at 4° C. for 10 minutes and the cell pellet washed once with phosphate-buffered saline.

The cell suspension was adjusted to a concentration of $10^7$ cells per ml in phosphate-buffered saline (PBS) containing 0.1% sodium azide and stored at 4° C. for further use.

EXAMPLE 2

Specific immuno-recognition of radiolabelled propranolol to an anti-propranolol solid phase McAb reagent according to the invention Hybridoma P-28: a cloned cell line producing monoclonal anti-propranolol antibodies, Hybridoma Dig 18: a cell line secreting monoclonal anti-digoxin antibodies; and NS1: the parental mouse myeloma cell line used in the creation of the hybridomas and which by itself does not secrete any complete immunoglobulin molecules, were each fixed as described in Example 1. Radioactive propranolol (4-$^3$H-propranolol, Amersham, specific activity=20 curies per m mole) at a concentration of 0.5 p mole or 150 pg per 0.1 ml per reaction was incubated with different amounts of the glutaldehyde fixed cells (0.1 ml) at room temperature for 1 hour. The mixtures were centrifuged at 3000 RPM at 4° C. for 20 minutes, the supernatants aspirated, and the cell pellet washed once with 1 ml of cold PBS. The washed cells were lysed in a total of 0.3 ml 0.1N NaOH and transferred to 3 ml of Pico-Fluor 30 scitillation counting solution.

Radioactivity was measured with a Tricard Scillilation Counter.

As shown in FIG. 1, only hybridoma P-28, the cell line that produced monoclonal antibodies to propranolol, binds specifically the radioactive antigen in a linear fashion, whereas both the McAb producing but non-relevant cell line (Dig 18) and the NS1 myeloma cells did not bind the labelled antigen probe.

EXAMPLE 3

Propranolol immunoassay using an anti-propranolol solid phase McAb reagent according to the invention A pre-determined amount of an anti-propranolol solid phase McAb prepared by the procedure of Example 1 ($2\times10^5$ cells per 0.2 ml), was incubated with different concentrations of propranolol dissolved in human serum (0.1 ml) for 1 hour at 37° C. $^3$H-propranolol was added at 150 pg per 0.1 ml per reaction and the reaction mixtures were further incubated at room temperature for 1 hour. The mixtures were centrifuged and the cells were washed as described in Example 1. After solubilization by 0.1M NaOH, the radioactivity associated with the cells were counted in a Tricarb scillilation counter. FIG. 2 shows a competition curve between 2 to 150 ng per ml of propranolol.

The uptake of radioactive propranolol by the above reagent according to the invention can be proportionally inhibited by the native McAb. Increasing amounts of mouse ascites fluid containing the McAb were incubated with 3 H-propranolol prior to the addition of the antibodies carrying hybridoma cells. As shown in FIG. 3, the residual radioactivity bound to the cells is inversely proportional to the amount of the McAb added. This is a further proof that the uptake $^3$H-propranolol by the cells is an antigen-antibody reaction, inhibited both by the native antigen or by free antibodies in suspension.

EXAMPLE 4

Immunoassay for digoxin with an anti-digoxin solid phase McAb reagent according to the invention Hybridoma Dig-18, a cloned cell line producing McAb to the drug digoxin, and NS1, the parental immunoglobulin non-secreting myeloma cell line, were fixed as described in Example 1. A constant amount of radioactive digoxin ($^{125}$I-Digoxin) was added to increasing amounts of the fixed cells and incubated at room temperature for 1 hour. The reaction mixtures were centrifuged at 3000 RPM for 20 minutes at 4° C., the supernatants were aspirated and the cell pellet washed once with 1 ml cold phosphate-buffer saline. The radioactivities associated with the washed cells were measured by a Packard gamma counter. FIG. 4 shows specific binding of $^{125}$I-Digoxin to Dig-18 cells, but negligible radioactivity could be detected with the NS1 cells.

A radioimmunoassay was developed using the Dig-18-McAb preparation according to the invention. A pre-determined amount of fixed Dig-18 cells ($1\times10^5$ cells per 0.1 ml) was added to different dilutions of digoxin in drug-free human serum (0.1 ml). After 30 minutes at room temperature, $^{125}$I-digoxin was added to all tubes and incubated for another 30 minutes. The mixtures were centrifuged, washed and counted as described above. FIG. 5 shows a standard curve, establishing the fact that increasing concentration of unlabelled digoxin will displace the amount of $^{125}$I-digoxin bound to the solid phase non-active Dig-18-McAb reagent according to the invention.

To prove that the incorporation of $^{125}$I-digoxin to the Dig-18-McAb preparation is indeed an antigen-antibody reaction, an inhibition curve was constructed using the soluble McAb produced in vitro as culture supernatant from Clone Dig-18 to compete with the solid phase antibodies for $^{125}$I-digoxin. Results as presented in FIG. 6 indicate that increasing concentrations of the soluble McAb inhibited the incorporation of $^{125}$I-digoxin to the preparation. This result supports the notion that the McAb as presented on the solid phase reagent are indeed reacting to the antigen in a manner competitive to the native, soluble McAb produced by the same hybridoma cell line.

EXAMPLE 5

Homogeneous Immunoassay for human serum albumin (HSA) using an anti-HSA solid phase McAb reagent according to the invention Hybridoma B-20, a cloned cell line producing monoclonal anti-HSA antibodies; hybridoma P-49, a cell line secreting monoclonal anti-propranolol antibodies and NS1, the parental mouse myeloma cell line, were fixed by the procedure according to Example 1, except that instead of glutaraldehyde, formaldehyde at a final concentration of 10% was used as the inactivator substance.

Fixed cells of clone B-20 containing immunologically active monoclonals have been used to develop a homogeneous, non-isotopic, one-step immunoassay as described below. A total of $5 \times 10^5$ formaldehyde-fixed hybridoma cells from clone B-20 in 50 μl PBS were incubated with fluorescein-labelled HSA (FITC-HSA; 2 μg HSA per 100 μl per reaction, molar ratio of FITC to HSA is 3.4) at room temperature for 1 hour. The entire reaction mixture was diluted to 1 ml with PBS and analyzed by a Becton Dickinson 440 Fluorescence Activated Cell Sorter (FACS). An argon laser (300 MW, 488 nm) was used for excitation. Hybridoma fixed cells were injected at a rate of 300–800 cells per second into a 80 μM PBS stream. Filters were used to permit emitted wavelength of >520 nm to be analyzed. To determine the number of positive fluorescence cells, a marker was set as a reference point to differentiate the specific stained fixed cells with that of the autofluorescence of the cells without the addition of the fluorescent conjugate. FIG. 7 shows positive staining of the majority (75%) of the population of anti-HSA McAb embedded hybridoma cells from clone B-20 (right side, solid line) by FITC-HSA, where a positively stained cell is classified as fluorescent beyond the reference point, as compared with the negative control (left side, dotted line), comprised of cells from clone B-20 and PBS alone (10% of cells above the reference point). When increasing amounts of non-labeled HSA (100 μl of sample in the concentration indicated per reaction) were added to the incubation mixture, containing B-20 cells and FITC-HSA, a shift in the peak towards the negative control was observed. A total of approximately 20,000 fixed cells were analyzed in each sample. Using the reference point, the number of positive fluorescent cells was determined for each HSA concentration used (Table I). The "percent fluorescent cells" in each sample was calculated as:

$$\frac{\text{Number of positive fluorescent cells above reference gate}}{\text{Total number of cells analyzed}} \times 100\%$$

Incubation of FITC-HSA with fixed hybridoma cells of anti-propranolol producing clone P-49 gave no significant positive fluorescence over the unstained P-49 cells (Table II). An inhibition standard curve profile can be constructed from data obtained in Table I by calculating the relative amount of positive cells (percent bound) in each sample (FIG. 8). In the presentation of the standard curve, the value of 100% was set for the sample containing only the fixed hybridoma cells and FITC-HSA conjugate. The relative percentage of FITC-HSA bound to the cells (percent bound) in the samples with different concentrations of added HSA was calculated accordingly. Thus, the amount of antigen present in any unknown sample can be obtained via this standard competitive inhibition curve.

The above results indicate that the uptake of fluorescence of the hybridoma cells from the fluorescein labelled antigen is indeed an immunological reaction as demonstrated by the proportional inhibition by unlabelled antigen. Furthermore, the sensitivity of the fluorescence flow cytometry together with the localized concentration of the McAb on the fixed hybridoma cells enables a direct assay of the reaction mixture without separating the excess fluorescence-labelled antigen in the sample from the "bound" fluorescence on the fixed cells. Similar results can be obtained via fluorescence microscopy.

EXAMPLE 6

One-step, non-isotopic, homogenous Immunoassay for serum propranolol

Hybridoma P-49, a cloned cell line producing monoclonal anti-propranolol antibodies, was fixed with formaldehyde as described in Example 5. A constant amount of FITC-labelled propranolol-BSA (4 nmole per 100 μl per reaction, molar ratio of FITC to propranolol is 0.3) was added to $5 \times 10^5$ fixed hybridoma cells (50 μl) from clone P-49, together with human serum standard samples containing different amounts of unlabelled propranolol as indicated (100 μl of serum standards per reaction). After incubation at room temperature for one hour, the entire reaction mixture is analyzed by FACS as described in Example 5. A proportional shift of the peak (representing the mean fluorescence of the majority of the cells in the sample) can be seen upon the addition of unlabelled propranolol in serum, as demonstrated by the decreasing number of fluorescent cells above the set reference gate (Table III).

These results indicate that the homogeneous, one-step immunoassay applies to small hapten molecules (such as propranolol) as well as macromolecules (such as HSA, see Example 5). Furthermore, clinical samples such as human serum can be analyzed by this direct, homogeneous method without interference to the analytical procedure.

TABLE I

Analysis of the inhibition of fluorescent HSA attached to the B-20 fixed hybridoma cells by unlabelled HSA via Fluorescent Flow Cytometry

| HSA added (μg/ml) | Total No. cells analyzed | No. of cells above reference gate |
|---|---|---|
| 0 | 21142 | 15977 |

TABLE I-continued

Analysis of the inhibition of fluorescent HSA attached to the B-20 fixed hybridoma cells by unlabelled HSA via Fluorescent Flow Cytometry

| HSA added (μg/ml) | Total No. cells analyzed | No. of cells above reference gate |
|---|---|---|
| 1 | 20207 | 15090 |
| 5 | 21794 | 16042 |
| 10 | 20519 | 12577 |
| 25 | 20689 | 11281 |
| 50 | 20131 | 3456 |
| 100 | 21623 | 2631 |
| 200 | 17049 | 1707 |

TABLE II

Specific Immuno-staining of McAb embedded fixed hybridoma cells according to the invention by the correspondent FITC-antigen

| "Non-active" hybridoma cells used | FITC-HSA added | Total No. cells analyzed | No. of cells above reference gate |
|---|---|---|---|
| B-20 (anti-HSA) | 2 μg | 20627 | 15842 |
| B-20 (anti-HSA) | 0 | 20241 | 3556 |
| P-49 (anti-propranolol) | 2 μg | 20098 | 1129 |
| P-49 (anti-propranolol) | 0 | 20629 | 2201 |

TABLE III

Homogeneous Immunoassay for serum propranolol using the solid phase McAb

| Propranolol Added (μM) | Total No. cells analyzed | No. cells above Reference gate |
|---|---|---|
| 0 | 20030 | 17900 |
| 0.05 | 20470 | 15730 |
| 0.1 | 20370 | 11600 |
| 0.5 | 20340 | 9009 |
| 1 | 20530 | 7830 |
| 2 | 20800 | 6800 |
| 10 | 23040 | 3000 |

EXAMPLE 7

Preparation of reagents according to the invention for colorimetric test

Two procedures were successfully carried out to colour solid phase McAb reagents according to the invention. They are both outlined below.

First procedure:
1. As described in Example 1, the prepared cells were fixed with a 2.5% v/v solution of glutaldehyde and incubated for 30 minutes at 4° C.
2. A 0.2% solution of trypan blue was added in a 1:1 volume and further incubated for 10 minutes.
3. The reaction mixture was centrifuged at 1200 RPM for 10 minutes at 4° C. and washed with phosphate-buffered saline (PBS).
4. Glycine was added and the mixture was incubated for 10 minutes at 4° C. and treated as in step No. 3.
5. The cell suspension was adjusted to $10^7$ cells/ml of PBS with 0.1% sodium azide and stored at 4° C.

Second Procedure:
In this method the colour was added only after the cells were treated with glycine and resuspended as in step No. 5 above.
1. A 0.2% solution of trypan blue was added (1:1) to the cells and incubated for 10 minutes at 4° C.
2. The reaction mixture was centrifuged at 1200 RPM for 10 minutes at 4° C. and washed with PBS.
3. The cell suspension was adjusted to $10^7$ cells/ml of PBS with 0.1% sodium azide and stored at 4° C.

Both protocols produced a cell suspension of deep blue colour and when settled showed a clear supernatant.

We claim:

1. A reagent for use in solid phase immunoassay diagnostics comprising a matrix of fixed hybridoma cells embedded with and covalently bound to its self-produced monoclonal antibodies, said bound monoclonal antibodies presenting sites available for binding to a specific antigen, and at least one auxiliary substance selected from the group consisting of labelling materials, dyes and color reagents for use in colorimetric tests.

2. A solid phase reagent according to claim 1 wherein said auxiliary substance is a member of the group consisting of dyes and colour reagents for use in colorimetric tests.

3. A solid phase reagent according to claim 1 wherein said auxiliary substance is an enzymatic labelling material.

4. A solid phase reagent according to claim 1 wherein said auxiliary substance is a fluorescent labelling material.

5. A solid phase reagent according to claim 1 wherein said auxiliary substance is a luminescent labelling material.

6. A solid phase reagent according to claim 1 wherein said auxiliary substance is a radioactive labelling material.

7. A solid phase reagent according to claim 1 mounted on a solid support.

8. A process for the preparation of a solid reagent for use in diagnostic immunoassay, comprising incubating in vitro a culture medium containing active hybridoma cells capable of producing monoclonal antibodies, allowing the formation of antibodies to proceed, separating and washing said cells free of serum, resuspending the cells in a buffer solution, adding a fixative to the resulting suspension, thus covelently binding to said hybridoma cells these self-produced monoclonal antibodies which were incapable of removal from said hybridoma cells by said washing and resuspending steps thereby to produce an immobilized fixed hybridoma cells/monoclonal antibodies complex, binding excessive free inactivator substance and isolating said immobilized fixed hybridoma cells/monoclonal antibodies complex.

9. A process according to claim 8 wherein said fixative is an aliphatic aldehyde.

10. A process according to claim 9 wherein said fixative is glutaraldehyde.

11. A process according to claim 8 wherein an auxiliary substance selected from the group consisting of labelling materials, dyes and color reagents for use in colorimetric tests is added to the reaction mixture.

12. A reagent for use in solid phase immunoassay diagnostics consisting essentially of a matrix of fixed hybridoma cells embedded with and covalently bound to its self-produced monoclonal antibodies, said bound monoclonal antibodies presenting sites available for binding to a specific antigen.

13. The reagent of claim 12, containing at least one auxiliary substance selected from the group consisting of dyes and color reagents for use in colorimetric tests and labelling materials.

* * * * *